United States Patent
Danteny

(10) Patent No.: US 8,452,386 B2
(45) Date of Patent: May 28, 2013

(54) EVENT DRIVEN AMBULATORY ELECTROCARDIOGRAPH

(75) Inventor: Alain Danteny, Saint Thibault Des Vignes (FR)

(73) Assignee: Parsys, Noisy le Grand Cedex (FR)

( * ) Notice: Subject to any disclaimer, the term of this patent is extended or adjusted under 35 U.S.C. 154(b) by 473 days.

(21) Appl. No.: 12/666,097

(22) PCT Filed: Jun. 25, 2008

(86) PCT No.: PCT/FR2008/051141
§ 371 (c)(1),
(2), (4) Date: Dec. 22, 2009

(87) PCT Pub. No.: WO2009/007592
PCT Pub. Date: Jan. 15, 2009

(65) Prior Publication Data
US 2010/0174204 A1   Jul. 8, 2010

(30) Foreign Application Priority Data

Jun. 26, 2007 (FR) ...................................... 07 56044
Jun. 26, 2007 (FR) ...................................... 07 56045
Jun. 26, 2007 (FR) ...................................... 07 56048

(51) Int. Cl.
*A61B 5/0404* (2006.01)
(52) U.S. Cl.
USPC ....................................................... 600/509
(58) Field of Classification Search
USPC ....................................................... 600/509
See application file for complete search history.

(56) References Cited

U.S. PATENT DOCUMENTS

| 4,573,474 A | 3/1986 | Scibetta |
| 5,010,888 A | 4/1991 | Jadvar et al. |
| 7,266,405 B1 * | 9/2007 | Alroy et al. .................... 600/386 |
| 2010/0168593 A1 * | 7/2010 | Sakoda et al. ................. 600/509 |

FOREIGN PATENT DOCUMENTS

| EP | 0611287 B | 11/1999 |
| EP | 1676528 A1 | 7/2006 |
| WO | WO 99/38436 | 8/1999 |
| WO | WO 2005/027720 A2 | 3/2005 |

* cited by examiner

*Primary Examiner* — Scott Getzow
*Assistant Examiner* — Amanda Patton
(74) *Attorney, Agent, or Firm* — Preti Flaherty Beliveau & Pachios LLP

(57) ABSTRACT

The electrocardiograph (200) of the invention is suitable for capturing a twelve-lead electrocardiogram from signals representative of the cardiac activity of a patient and acquired with the help of at least nine electrodes. The electrocardiograph comprises a body (210) having a front face (211) and at least one arm (212, 213) suitable for being folded beside the body and pivotable about an axis that is substantially parallel to the front face. Each arm is adapted to form a variable dihedral angle with the front face so that the substantially concave surface (214) formed by the front face and the or each arm and having six precordial electrodes (201-206) distributed thereon, is capable of adapting to the patient's morphology so as to enable the precordial electrodes to be properly positioned on the patient's chest. The electrocardiograph also includes means enabling said good positioning of the precordial electrodes on the patient's chest to be maintained.

22 Claims, 7 Drawing Sheets

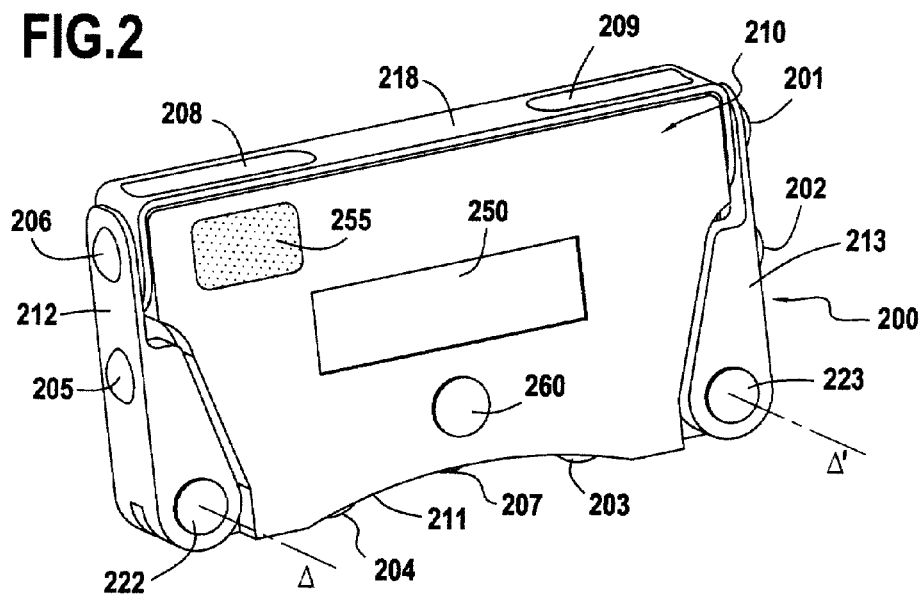
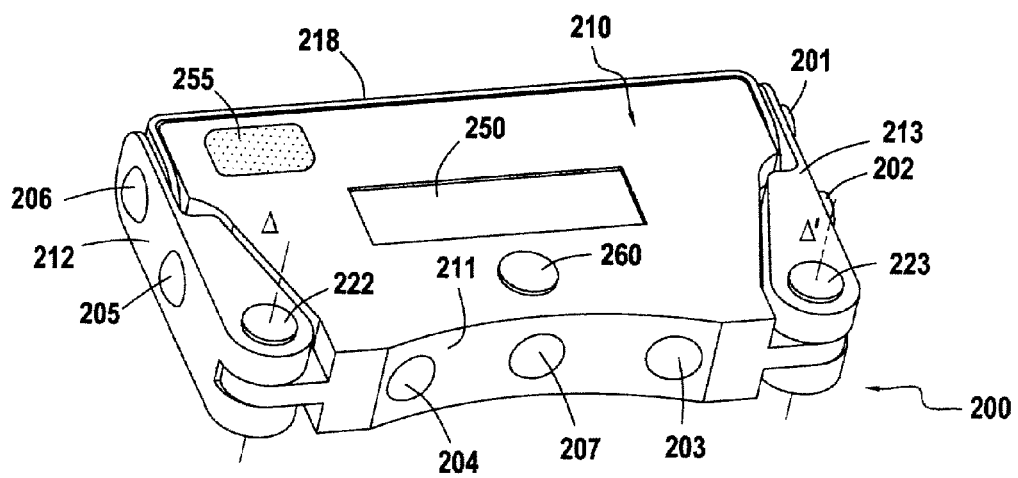

EVENT DRIVEN AMBULATORY ELECTROCARDIOGRAPH

BACKGROUND OF THE INVENTION

The present invention relates to the general field of electrocardiographs.

More particularly, the invention relates to an event-driven ambulatory electrocardiograph. Such a device makes it possible, advantageously, for a patient to record his or her own emergency electrocardiogram, e.g. at home, in the event of a supposed attack and without the presence or the assistance of any qualified medical personnel. It needs to be compact and simple to handle so that it can be positioned easily on the patient's chest in a position that is sufficiently stable to ensure good acquisition of signals, but without giving rise to additional stress for the patient.

Document EP 0 611 287 B1 describes a portable electrocardiograph enabling a twelve-lead electrocardiogram to be captured from the signals acquired by nine electrodes. A twelve-lead electrocardiogram enables various forms of cardiac or cardiovascular pathologies to be diagnosed such as arrhythmia or repolarization anomalies.

The signals representative of the patient's cardiac activity may be stored in the electrocardiograph in order to reproduce the electrocardiogram on a recording strip. They may also be converted into acoustic signals and transmitted by a loudspeaker over a telephone line to a remote center.

In the embodiment shown in FIG. 1A, the portable electrocardiograph 100 of document EP 0 611 287 B1 has a housing with a rigid support surface 114 with six precordial electrodes 101-106 placed thereon for application on the respective points V1-V6 of the patient's chest.

The support surface 114 is concave. In the meaning of the invention, a surface is "concave" or "substantially concave" when it is suitable for fitting around the curved chest of a patient, and is not necessarily a concave surface in the mathematically strict sense. Specifically, the concave surface 114 of the electrocardiograph 100 is made up of three sections, namely a main support 111 and two lateral supports 112 and 113, each lateral support being at a fixed angle $\alpha$, $\beta$ relative to the main support 111.

It is not easy for a patient using such a device to position the precordial electrodes on the chest, particularly while suffering an attack. In particular, the electrocardiograph 100 does not enable "perfect" contact to be guaranteed between the precordial electrodes and the precordial points of the patient's chest, in order to capture the electrocardiogram correctly. Unfortunately, the quality of the recorded electrocardiogram depends to a very large extent on the conditions with which the electrodes are applied to the patient's body, and in particular the precordial electrodes that are the most sensitive to poor positioning. In the event of poor positioning, and in particular poor contact between the electrodes and the corresponding precordial points, the electrical signals acquired by the electrodes may be greatly disturbed and unsuitable for enabling the electrocardiogram as captured in this way to be used in satisfactory manner.

This is particularly damaging when these signals of poor quality are transmitted over a telephone line in order to enable the electrocardiogram to be produced by a remote center, since the patient is not in a position to see immediately that the electrocardiogram is useless. Furthermore, the cost of the telephone call is a pure loss.

In order to minimize that difficulty, document WO 99/38436 proposes an ambulatory electrocardiograph having three precordial electrodes, with an embodiment thereof being shown in FIG. 1B. That device 120 enables an electrocardiogram to be recorded having eight leads instead of the conventional twelve.

The electrocardiograph 120 in that embodiment is provided with two arms 122 and 123, each provided with a precordial electrode (124 and 125 respectively) at its end. The third precordial electrode is situated on the bottom face 121.

The arms 122 and 123 are capable of pivoting about respective ball joints defined by axes $\delta$ and $\delta'$ perpendicular to the bottom face 121 so as to be folded down onto the top face of the electrocardiograph 120. This enables the size of the electrocardiograph 120 to be reduced while it is not in use.

Nevertheless, it is not possible for an eight-lead electrocardiogram of the kind described in document WO 99/38436 to be analyzed by a person who has not been trained in interpreting such results, such as an emergency doctor or a general practitioner, when such a person is in the habit of interpreting twelve-lead electrocardiograms. Furthermore, the regulations presently in force in France (in particular for the Social Security services) do not recognize the use of such electrocardiographs.

OBJECT AND SUMMARY OF THE INVENTION

A main object of the present invention is to mitigate the above-mentioned drawbacks.

More precisely, the invention provides an event-driven ambulatory electrocardiograph adapted to capture a twelve-lead electrocardiogram from analog electrical signals representative of the cardiac activity of a patient and acquired by means of at least nine electrodes, said electrocardiograph comprising a main support and at least one lateral support having six precordial electrodes distributed thereon, each lateral support forming an angle relative to the main support such that the main support and the lateral supports define a surface that is substantially concave. In accordance with the invention, the main support of the electrocardiograph of the invention is a front face of an electrocardiograph body and each lateral support is an arm capable of being folded down along the side of the body and of pivoting about an axis that is substantially parallel to the front face, each arm being adapted to form a variable dihedral angle relative to the front face.

The substantially concave surface can thus be adapted to the patient's morphology and can enable the precordial electrodes to be properly positioned on the patient's chest.

In accordance with the invention, the electrocardiograph of the invention also includes means enabling the precordial electrodes to be kept properly positioned on the patient's chest.

Thus, by using pivotable arms carrying precordial electrodes (and no cable) that are capable of forming a variable dihedral angle relative to the front face of the body of the electrocardiograph, the electrocardiograph of the invention enables an electrocardiogram to be captured for patients presenting morphologies that are different. This is done merely by applying the electrocardiograph against the chests of patients. Proper positioning of the precordial electrodes on the patient's chest, and in particular the quality of contact between said electrodes and the corresponding points of the chest, is ensured firstly by the use of such arms and secondly by means that enable said good positioning and good contact to be maintained. This enables an electrocardiogram of good quality to be captured.

In a particular embodiment, each arm of the electrocardiograph of the invention is fitted with a respective spring. The spring imparts a certain amount of "resilience" to the arm about a dihedral angle that matches the patient's morphology.

This resilience enables the precordial electrodes to be kept in contact with the precordial points of the patient's chest and to ensure that, once the electrodes have been properly positioned, the signals that are sent are stable. Specifically, this makes it possible to avoid exerting extra pressure on the precordial electrodes in order to guarantee that they are in contact with the patient's chest, where such pressure can disturb capture of the electrocardiogram.

Furthermore, since each arm can be folded along the side of the body, the electrocardiograph of the invention is compact.

In a particular embodiment of the invention, the twelve leads of the electrocardiogram are acquired simultaneously, i.e. the electrocardiograph of the invention is a "12 lead-12 channel" electrocardiograph. This makes it possible to deliver an electrocardiogram that is precise, and useful for diagnosing cardiac anomalies, having twelve leads capturing the cardiac activity of the patient simultaneously.

The electrodes of the electrocardiograph of the invention are preferably dry electrodes. Unlike electrodes with gel or sticky electrodes, such electrodes do not require any preparation of the skin or any application of gel (e.g. electrolytic gel). This makes it possible to avoid the side effects usually observed with electrodes associated with gel or sticky electrodes, such as problems of irritation or allergy.

In a particular embodiment, the electrocardiograph of the invention includes an arm having at least one precordial electrode.

In a preferred embodiment, the electrocardiograph of the invention has two arms on either side of the body, each arm being provided with two precordial electrodes.

By way of example, the positioning of the precordial electrodes on the two arms and on the front face of the electrocardiograph of the invention may be as follows:

the two precordial electrodes of one of the arms correspond respectively to the points V1 and V2 of the patient's chest;

the two precordial electrodes of the other one of the arms correspond respectively to the points V5 and V6 of the patient's chest; and the front face of the body of the electrocardiograph is provided with two precordial electrodes corresponding respectively to the points V3 and V4 of the patient's chest.

Merely by applying the electrocardiograph to the patient's chest the electrocardiograph of the invention thus makes it possible to acquire directly the precordial leads V1 to V6 known to the person skilled in the art.

In a particular embodiment of the invention, two out of the nine electrodes of the electrocardiograph of the invention serve to acquire signals relating to the upper limbs of the patient.

Preferably, these two electrodes are disposed on the electrocardiograph in such a manner as to enable the index or middle fingers of the patient to be applied on the two electrodes when the six precordial electrodes are in position on the chest of the patient.

Advantageously, this enables the patient to get a good grip on the electrocardiograph and to hold it well for capturing an electrocardiogram while nevertheless keeping a relaxed position. In particular, this makes it possible to avoid the patient having tense shoulder muscles, which could give rise to interfering signals while capturing the electrocardiogram.

In a particular embodiment of the invention, one of the nine electrodes of the electrocardiograph of the invention is a spoon or paddle type electrode located at the end of a cord attached to the electrocardiograph and enabling the signal to be acquired that relates to the lower left limb of the patient.

Such an electrode guarantees better contact with the patient's body than does a pin electrode, since such an electrode rolls easily. In position, it is easy to keep a spoon or paddle electrode pressed against the patient's body with the help of undergarments, so as to acquire the signal that relates to the patient's lower left limb.

In a particular embodiment of the invention, the electrocardiograph further includes, in addition to the nine electrodes, a neutral electrode positioned on the front face of the body of the electrocardiograph so as to be applied beneath the patient's left nipple.

This electrode replaces the right lower limb electrode conventionally used as a neutral electrode in prior art electrocardiographs. Like the precordial electrodes, the neutral electrode does not have a cable and is preferably dry.

Given its position, it may also constitute a marker for the patient for use in positioning the electrocardiograph of the invention on the chest. In a variant, the electrocardiograph of the invention may include a marker that can be seen or felt so as to enable the patient to position the electrocardiograph properly on the chest.

In a particular embodiment, the event-driven ambulatory electrocardiograph of the invention includes, for each of its electrodes:

means for converting the analog signal acquired by the electrode into a digital signal;

means for storing the digital signal; and means for converting the digital signal into an analog signal and means for directing the analog signal to a socket compatible with a first connector of a strand having a second connector that is compatible with a second electrocardiograph.

The analog signals of an electrocardiograph can thus be delivered to a traditional electrocardiograph that is suitable for delivering the above-mentioned twelve leads.

In this type of use, the patient who has captured his or her own electrocardiograph in ambulatory manner can take the electrocardiograph to a doctor for connection to the doctor's own electrocardiograph in order to obtain the electrocardiogram.

In a particular embodiment, the ambulatory event-driven electrocardiograph of the invention comprises:

means suitable for determining whether the analog signals have characteristics corresponding to at least one QRS complex, with such signals being said to be "in conformity"; and, where appropriate a memory suitable for storing the signals in conformity.

Thus, and most advantageously, the electrocardiograph does not store the signals obtained by the electrodes so long as they are not in conformity, in particular when they have not yet become stabilized while the electrocardiograph is being positioned or braced against the patient's chest, or in the event of the patient making large or sudden movements during acquisition.

The characteristics of a QRS complex may for example be characteristics of duration and amplitude. The person skilled in the art knows these characteristics and they are not recalled here.

This guarantees that the signals stored are of quality that is good enough to enable a usable electrocardiogram to be delivered.

In one embodiment, the electrocardiograph of the invention includes filter means for filtering the signals that are in compliance.

By way of example, the filter means are adapted at least to eliminate interfering signals or to stabilize the base line. Specifically, they may implement the known Pan Tompkins algorithm.

In a particular embodiment, the ambulatory event-driven electrocardiograph of the invention further includes:
- telecommunications means suitable for transmitting the signals in conformity or the filtered signals to a remote center from the memory; and
- control means suitable for triggering the transmission on detecting at least one predetermined event.

Most advantageously, the electrocardiograph transmits to the remote center only signals that can be used.

In a particular embodiment, the control means are adapted to trigger transmission as soon as said signals have been determined as being in conformity, or as soon as they have been filtered.

In other words, if the signals acquired by the electrodes are not usable, they are not transited to the remote center.

In a particular embodiment, the control means are adapted to trigger transmission after the electrocardiograph of the invention has received a command for that purpose.

Such a command may be issued in particular by the remote center when it has detected an error in the signals it has previously received, e.g. as a result of a transmission error.

The signals are preferably stored in the electrocardiograph of the invention while waiting for such a command, if any. In a particular embodiment of the invention, the memory contains signals corresponding to a plurality of acquisitions. Preferably when the memory is saturated, the signals of the most recent acquisition overwrite the signals of the oldest acquisition.

In a particular embodiment, the control means are suitable for preventing the above-mentioned transmission.

This mode serves to force preservation of the signals in the memory. It may be used in particular when the patient intends to visit the doctor in order to provide the doctor with the signals corresponding to a particular acquisition.

In a particular embodiment, the electrocardiograph of the invention includes secondary means for obtaining a plurality of signals representative of the cardiac activity of a patient and coming from another device.

This embodiment serves in particular to store or to transmit signals that are acquired using some other device, e.g. an electrode belt.

This embodiment thus enables remote monitoring of the patient to be established.

In a particular embodiment, the secondary means comprise a plurality of sockets, each socket being compatible with a connector of a strand suitable for conveying an analog signal obtained by the device.

In particular, this enables the patient to perform an acquisition with an electrode belt after taking care to connect the connectors of the belt strands in the sockets of the electrocardiograph of the invention in order to transmit the signals acquired by the belt to the remote center.

In a particular embodiment, the event-driven ambulatory electrocardiograph of the invention further includes means for displaying a message representative of the good and/or poor positioning of the electrodes.

This display may reassure the patient and thereby lower the patient's stress level, thus benefiting the quality of the signals that are acquired.

The invention also provides a system for remotely monitoring the cardiac activity of a patient, the system comprising:
- an electrocardiograph as mentioned above, in which the telecommunications means are constituted by means for wireless telecommunication with a base connected to a telecommunications network; and
- the base.

This provides an electrocardiograph that is very flexible to use since the patient is not obliged to be beside a network jack, typically a telephone jack in order to perform acquisition.

By way of example, the wireless telecommunications means comply with the Bluetooth (registered trademark) standard.

In a particular embodiment, the monitoring system of the invention further includes portable equipment suitable for establishing a voice call with a remote operator via said base. Such equipment may in particular be in the form of a medallion.

The remote operator can thus guide the patient in the use of the electrocardiograph and reassure the patient if stressed. This call may also be a Bluetooth (registered trademark) call.

BRIEF DESCRIPTION OF THE DRAWINGS

Other characteristics and advantages of the present invention appear from the following description made with reference to the accompanying drawings that show an embodiment having no limiting character. In the figures:

FIG. 2 is a first perspective view of an electrocardiograph of the invention, when its arms are folded against either side of the body, in one particular embodiment;

FIG. 3 is a second perspective view of the electrocardiograph of the invention, when its arms are folded against either side of the body, in one particular embodiment;

DETAILED DESCRIPTION OF SEVERAL EMBODIMENTS

Figure 1A:
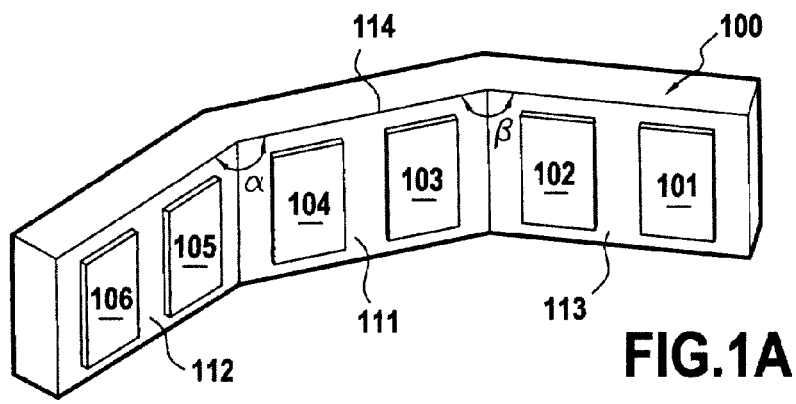
FIG. 1A, described above, is a diagrammatic view of a prior art device described in document EP 0 611 287 B1, in one particular embodiment.
Figure 1B:
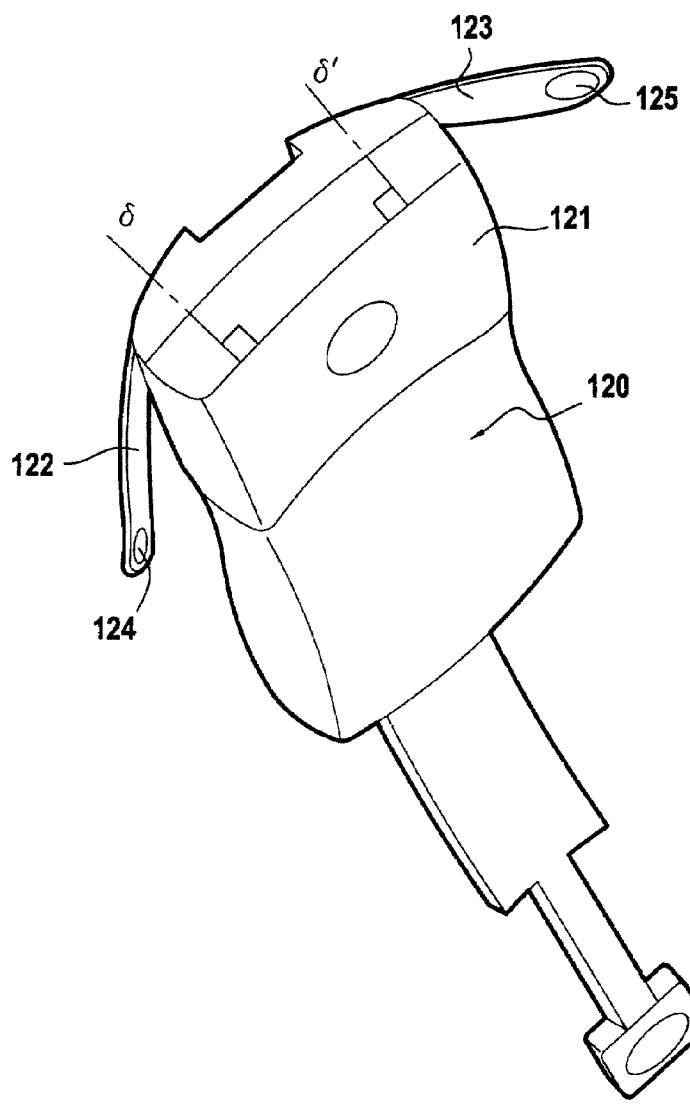
FIG. 1B, described above, is a diagrammatic view of a prior art device described in document WO 99/38436 in one particular embodiment.
Figure 4:
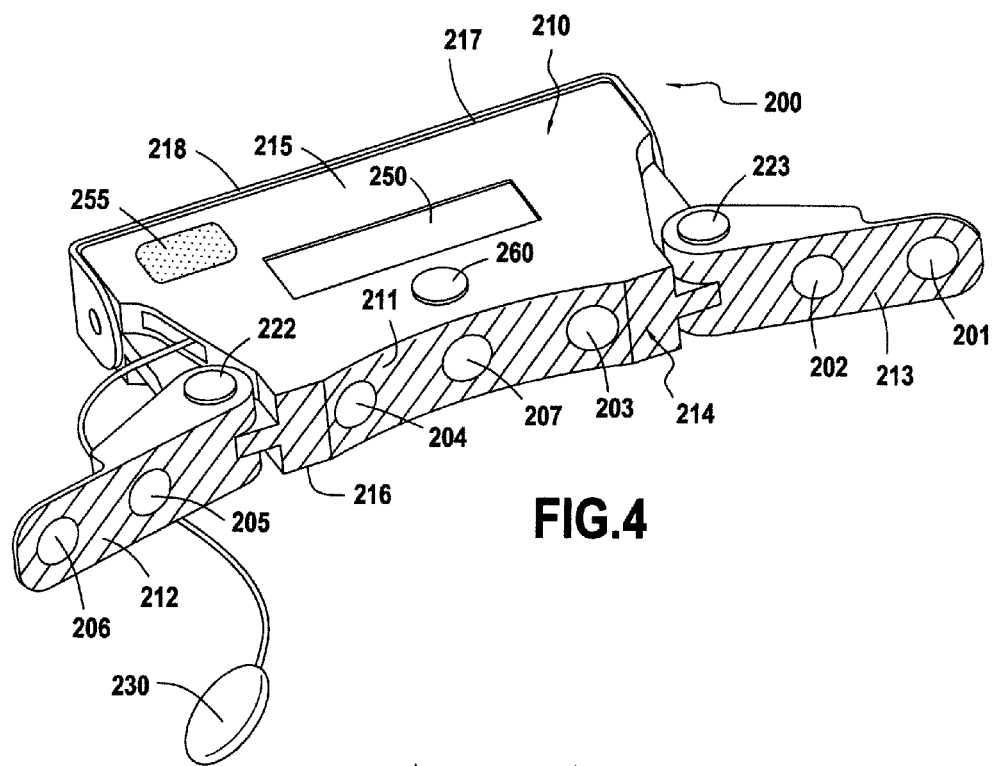
FIG. 4 is a third perspective view of the electrocardiograph of the invention, in particular when its arms are unfolded, in one particular embodiment.

FIGS. 2, 3, and 4 show an event-driven ambulatory electrocardiograph 200 in accordance with the invention in one particular embodiment. Such an electrocardiograph enables a patient to record his or her own emergency electrocardiogram, e.g. at home, in the event of a supposed attack, and without requiring assistance from qualified medical personnel.

The electrocardiograph 200 of the invention comprises a body 210 having in particular a front face 211, a top face 215, a bottom face 216, and a rear face 217. In the presently-described example, the front face 211 is itself a substantially concave surface having three electrodes 203, 204, and 207 placed thereon. It constitutes a main support in the meaning of the invention. In a variant, the front face 211 may be plane.

In the presently-described example, the electrocardiograph 200 also has two arms 212 and 213 (lateral supports in the meaning of the invention) capable of being folded down against the body 210. These arms 212 and 213 are hinged: each arm is adapted to pivot about a pivot axis that is substantially parallel to the front face 211, so as to form a variable dihedral angle with the front face 211. Thus, the arm 212 is pivotable about the axis Δ, while the arm 213 is pivotable about the axis Δ'.

This pivoting about the axes Δ and Δ' is made possible in the presently-described example by respective pins 222 and 223. By way of example, FIGS. 2 and 3 show the arms 212 and 213 in the folded-down position, e.g. when the electrocardiograph 200 is not in operation or in electrocardiogram-capture mode. In FIG. 4, the arms 212 and 213 are shown in the unfolded position, when the electrocardiograph 200 is ready to be used for capturing an electrocardiogram. In such a position, the arm 212, the front face 211, and the arm 213 form a substantially concave surface 214 that is shown shaded in FIG. 4.

In the presently-described example, two electrodes 201 and 202 or 205 and 206 are placed on each of the arms 213 or 212 respectively. Like the electrodes 203, 204, and 207 placed on the front face 211, the electrodes 201, 202, 205, and 206 are dry electrodes in this example. Such electrodes are known to the person skilled in the art and they are not described in greater detail herein. Each electrode is made of chromium-plated brass and in the presently-described example it presents a diameter of about 20 millimeters (mm). These electrodes do not have a cable.

Figure 5:
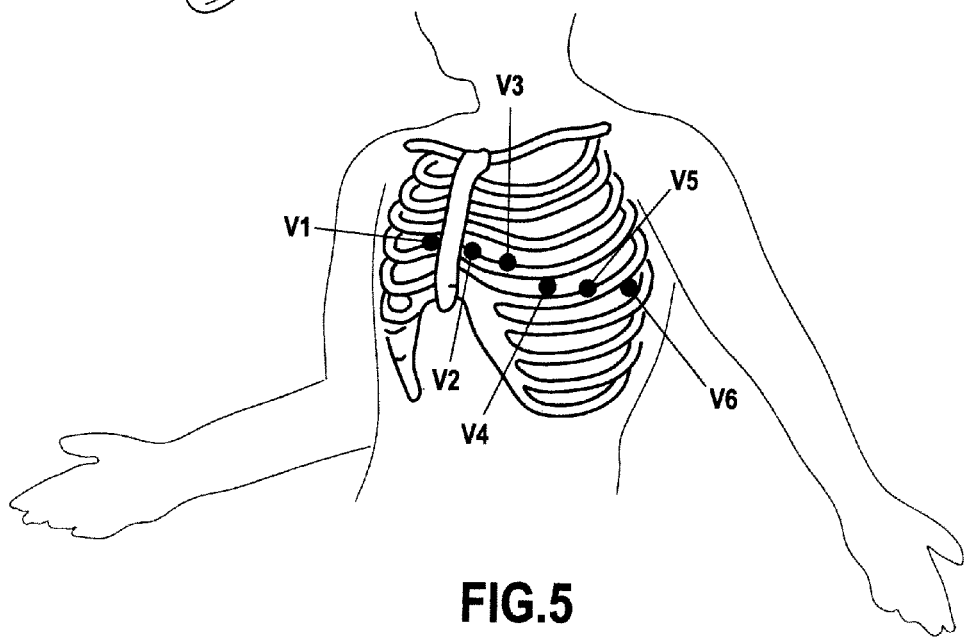
FIG. 5 shows the positioning of precordial points V1 to V6 on the chest of a patient.

The electrodes 201, 202, 203, 204, 205, and 206 are precordial electrodes for placing on the points V1 to V6 respectively of the precordial area of the patient's chest. The arrangement of these points is known to the person skilled in the art and is shown in FIG. 5.

Thus, the positioning of the electrodes on the arms 212 and 213, and on the front face 211, or in equivalent manner on the substantially concave surface 214, is such that the electrodes 201, 202, 203, 204, 205, and 206 can be put into contact with the patient's points V1 to V6 in order to capture an electrocardiogram. The hinge arms 212 and 213 form variable dihedral angles on either side of the front face 211 (angles φ and ψ shown in FIG. 6) so as to be capable of adapting to the patient's morphology so that the electrodes are properly positioned on the precordial points V1 to V6 of the patient.

The electrode 207 placed on the front face 211 halfway between the precordial electrodes 204 and 203 constitutes a so-called "neutral" electrode used for calculating the twelve leads of the electrocardiogram (D1, D2, D3, aVR, aVL, aVF, V1, V2, V3, V4, V5, V6) using principles that are known to the person skilled in the art. In this example it is situated at the center of the front face 211.

In order to maintain proper positioning of the electrodes on the precordial points V1 to V6 and in particular in order to maintain "perfect" contact between the electrodes and the patient's chest at these precise points, the electrocardiograph 200 also includes means for maintaining this proper positioning. This makes it possible to ensure that the electrocardiogram is captured correctly by minimizing or eliminating interfering signals associated with poor contact between the electrodes and the patient's chest. In the presently-described example, these means comprise two springs, or more precisely a respective spring associated with each of the arms, as shown in FIG. 6 and described below.

The springs 242 and 243 are associated with the arms 212 and 213 respectively. Each spring is fastened via a "stationary" end to the body 210 of the electrocardiograph 200 and via its opposite end to the arm with which it is associated. This opposite end is "movable" because of the freedom of the arms 212 and 213 to move about their respective pivot axes.

Figure 6:
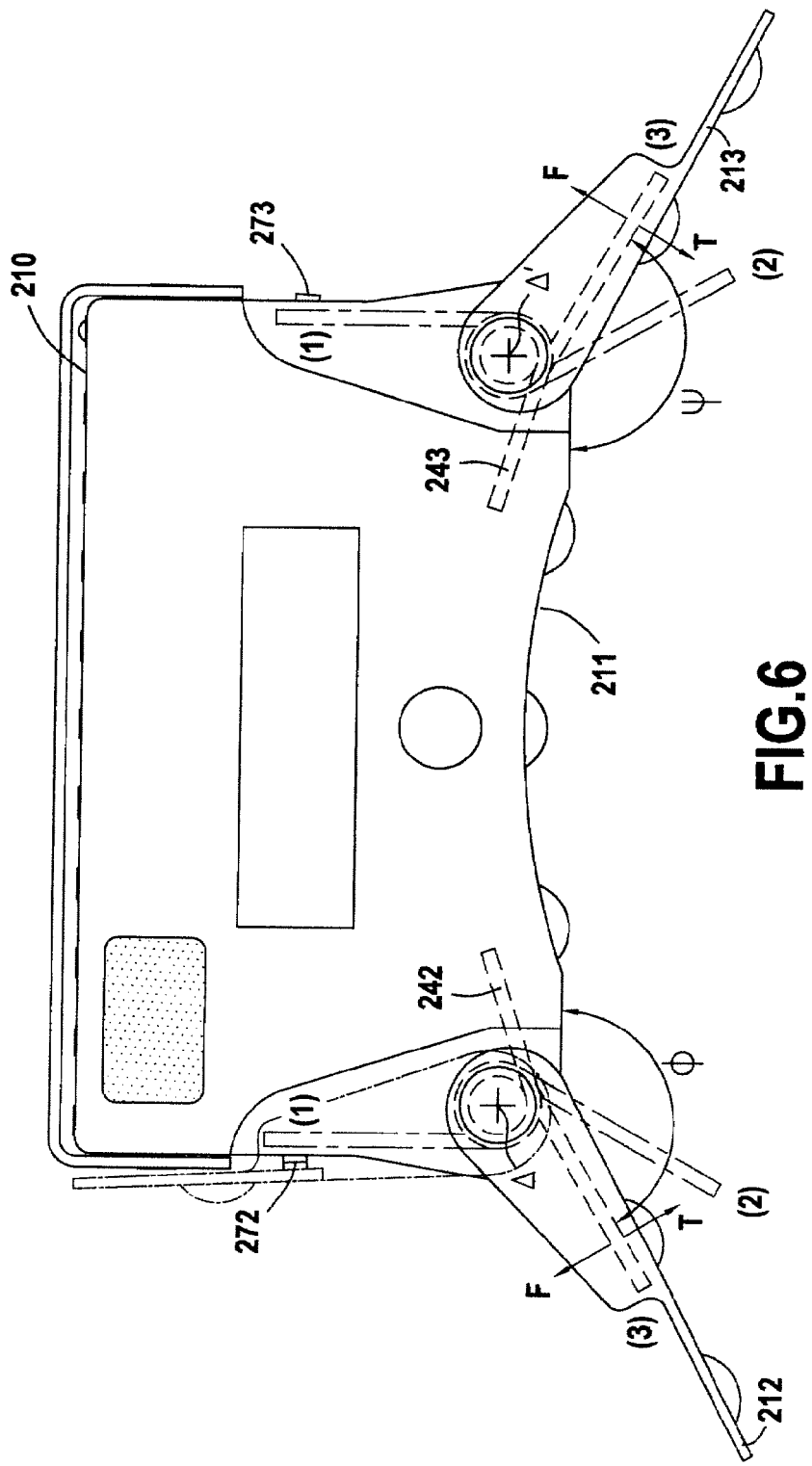
FIG. 6 is a plan view of the electrocardiograph of the invention in one particular embodiment, showing a plurality of positions for the arms of the electrocardiograph.

With reference to FIG. 6, when the springs 242 and 243 are at rest, the arms are in the position referenced (2).

When the electrocardiograph 200 is not in operation or in electrocardiogram-capture mode, the arms 212 and 213 are brought back beside the body 210 in a position referenced (1). This position is held, e.g. in this example with the help of two magnets 272 and 273 located on either side of the body 210 and serving to exert a force opposing the tension T of the spring. When the electrocardiograph 200 is put into operation, e.g. by the patient pressing on an ON button, the action of the magnets 272 and 273 is canceled, thereby enabling the arms 212 and 213 to be released so that they take up their rest positions (2).

When the electrocardiograph 200 is applied to a patient's chest, a force F is exerted by the patient's chest against the tension T from the springs 242 and 243, such that the arms associated with the springs 242 and 243 are held away from their rest positions (2) in respective stressed positions (3). The arms 212 and 213 then form respective dihedral angles φ and ψ relative to the front face 211. This makes it possible to guarantee good contact between the electrodes situated on the arms and the patient's chest, regardless of the patient's morphology. In this example, the rest position for each spring is determined upstream during manufacture of the electrocardiograph 200 so as to enable this operation to be achieved whatever the patient's morphology.

In another embodiment of the invention, in order to maintain proper positioning of the electrodes on the patient's chest, it is also possible to use a ratchet device associated with each of the arms (e.g. a ratchet wheel on each arm).

The electrocardiograph 200 also has a cap 218 fastened to the body 210 and hinged relative to said body 210 so as to be capable of being tilted towards the bottom face 216. In this example, the bottom face 216 of the electrocardiograph 200 is by definition the face opposite from the top face 215 (cf. FIG. 4).

At each of its ends (cf. FIG. 2) the cap 218 has disposed thereon respective peripheral electrodes 208 and 209 that are designed to acquire signals relating to the upper limbs of the patient (left upper limb VL and right upper limb VR). In the presently-described example, the electrodes 208 and 209 are dry metal electrodes of chromium-plated brass without a cable. They are oblong in shape so that the patient can press the index or middle fingers thereagainst. This serves advantageously to enable the patient to hold the device 200 in stable manner with the muscles of the shoulders relaxed, so as to capture a good electrocardiogram once the six precordial electrodes are properly positioned on the six precordial points V1 to V6.

The electrocardiograph 200 also has a third dry peripheral electrode 230, that is preferably of the spoon or paddle type located at the end of a metal cord that is attached to the electrocardiograph 200 (cf. FIG. 4). This electrode is applied in the region of the groin to acquire the signal relating to the left lower limb (VF). In the presently-described example, the metal cord having the electrode 230 at its end may be reeled for storage into the inside of the body 210 when the electrocardiograph 200 is not in operation, e.g. passing through a slot formed in a side face of the body 210 of the electrocardiograph 200 (under the arm 212 when it is in its folded-down position).

In another embodiment of the invention, a pin type dry electrode may also be used as a peripheral electrode in order to acquire the signal relating to the lower left limb (VF).

The six precordial electrodes 201 to 206, the three peripheral electrodes 208, 209, and 230, and the "neutral" electrode 207 are used for acquiring signals representative of the patient's cardiac activity enabling the event-driven ambulatory electrocardiograph 200 to deliver a twelve-lead electrocardiogram. In the presently-described example, it is assumed that the twelve leads are acquired (via the ten electrodes) and delivered simultaneously. This makes it possible to deliver an electrocardiogram that is very precise, for which the various leads represent a capture of the patient's cardiac activity at the same instant. This can be referred to as a "12 lead and 12 channel" electrocardiograph.

The electrocardiograph 200 also has a graphics screen 250 for displaying messages, in particular to indicate that the electrodes are wrongly positioned. For example, the electrocardiograph 200 has means for analyzing the signal received via the electrodes and for detecting whether one of the electrodes is not in contact with the patient's body. Where appropriate, a message indicative of this poor positioning is displayed on the screen 250. Other types of message may be displayed on the screen, such as for example messages associated with the use of the appliance.

These messages are also delivered via loudspeaker 255 located in the top face 215 of the body 210.

The electrocardiograph 200 also has an ON/OFF button 260 for switching the electrocardiograph 2000N in order to capture an electrocardiogram, or for switching it OFF. As mentioned above, when the patient presses on this button 260, the magnets 272 and 273 are deactivated such that the arms 212 and 213 take up a rest position, ready to be positioned on the patient's chest so that the six precordial electrodes 201-206 are put into contact with the points V1-V6.

Figure 7:
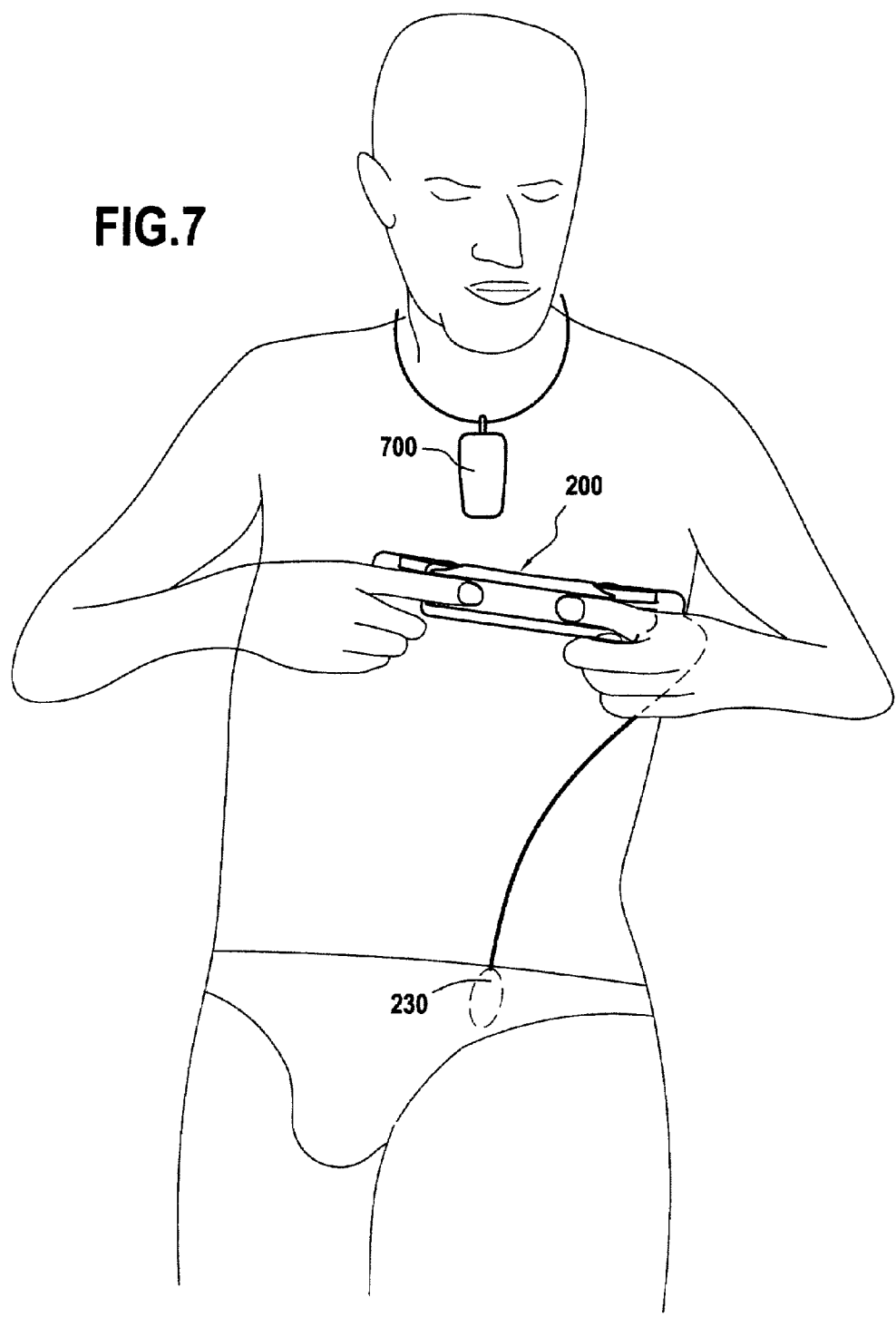
FIG. 7 is a diagrammatic view showing the positioning of the electrocardiograph of the invention while it is in use for capturing an electrocardiogram, in one particular embodiment.

FIG. 7 is a diagram showing the use of the electrocardiograph 200. The patient presses the electrocardiograph 200 of the invention against the chest, holding it in both hands. The peripheral electrode 230 is placed in the patient's left groin. The neutral electrode 207 is placed under the patient's left nipple.

In a variant, the electrocardiograph 200 may include a marker that is visible or that is in relief on its top face 215 enabling the patient to position the neutral electrode 207 in the proper place (e.g. by placing the visual marker under the left nipple).

While the electrocardiograph 200 is being applied against the patient's chest, its arms 212 and 213 are splayed apart from their rest positions so as to form respective dihedral angles relative to the front face 211 to match the patient's morphology. The dihedral angles between the arm 212 and the front face 211 (angle φ) and between the arm 213 and the front face 211 (angle ψ) are such that the electrodes 201 to 206 are positioned on the points V1 to V6 of the patient's chest. The patient presses both index fingers or both middle fingers on the peripheral electrodes 208 and 209 in order to hold the appliance securely.

In order to ensure good contact between the precordial electrodes 201-206 and the points V1-V6, tests are carried out concerning the positioning of each electrode. In the event of any one of the electrodes being poorly positioned, a message is displayed on the graphics screen 250.

Once each electrode has been correctly positioned, the electrocardiograph 200 acquires the signals associated with each electrode so as to deliver the twelve leads of the electrocardiogram.

In the presently-described embodiment, the device 200 of the invention has two arms on either side of the body 210. Nevertheless, in a variant, in another embodiment of the invention, the electrocardiograph 200 could have only one arm. The electrodes 201 to 206 are then distributed differently so that they can be applied against the precordial points V1 to V6.

Furthermore, in another embodiment of the invention, the precordial electrodes of the electrocardiograph of the invention are used to acquire signals relating to points on the patient's chest that are different from the points V1 to V6. Suitable digital processing is then implemented to deliver a twelve-lead electrocardiogram enabling a doctor to diagnose anomalies.

Figure 8A:
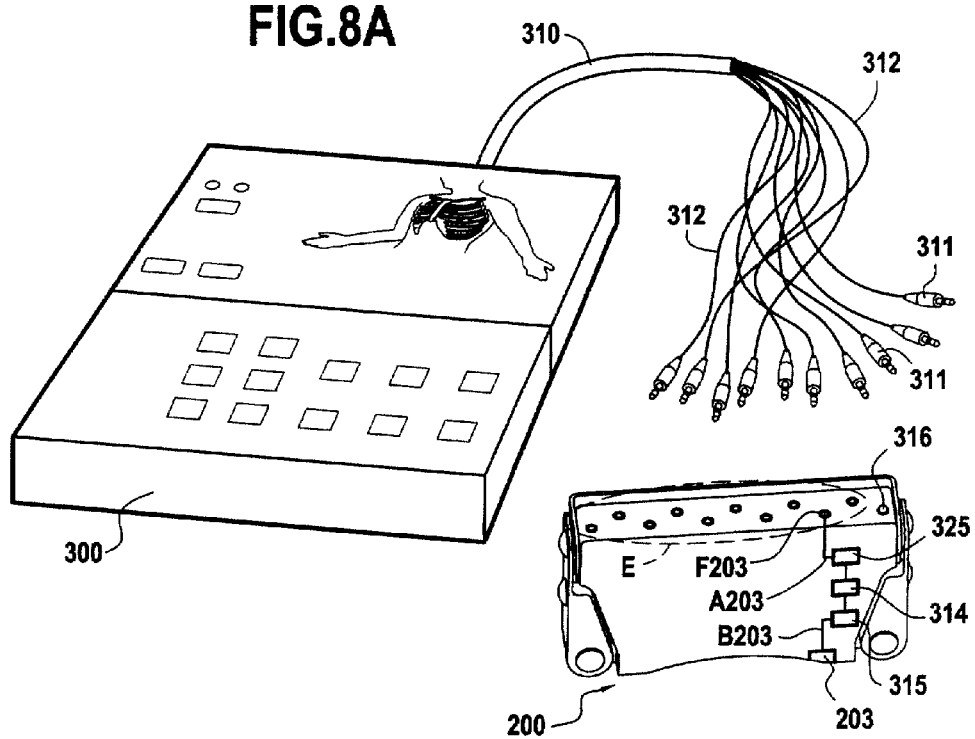
FIG. 8A shows an electrocardiograph in accordance with the invention in one particular embodiment.

FIG. 8A shows an electrocardiograph 200 in accordance with a particular embodiment of the invention.

For each of its electrodes, this embodiment has means for directing the analog signal obtained by said electrode to an analog-to-digital converter 315. The digitized signals are then stored in a rewritable non-volatile memory 314.

When the user presses on a button 316, the digitized signal corresponding to each of the electrodes is read from the memory 314 and converted into an analog signal by a digital-to-analog converter 325.

The analog signal is delivered to a socket compatible with a first connector 311 of a strand 312 having a second connector (not shown) that is compatible with another electrocardiograph 300.

In the presently-described embodiment, all of the strands 312 are grouped together in a common cable 310.

In the presently-described embodiment, the electrocardiograph 200 has two electrodes similar to the electrodes 201 to 209 and 230 as described above. For reasons of clarity, only the electrode 203 is shown in FIG. 8A.

The electrocardiograph 200 thus comprises a set E of ten sockets each being connected to one of the electrodes 201 to 209 and 230.

For reasons of clarity, this figure shows:
the electrode 203;
the electrical connection B203 between said electrode and the analog-to-digital converter 315;
the rewritable non-volatile memory 314;
the digital-to-analog converter 325; and
the electrical connection A203 between the converter 325 and the socket F203 corresponding to said electrode 203.

Thus, the two analog signals obtained by the electrodes 201 to 209 and 230 can be input to the electrocardiograph 300, which is itself capable of playing back the twelve leads of the electrocardiograph corresponding to these signals.

Thus, the analog signals may be input to the electrocardiograph 300 at some time after they were acquired, so long as the content of the memory has not been deleted or overwritten by a new acquisition. In one particular embodiment, the memory 314 is of capacity that is sufficient to store the signals from a plurality of acquisitions.

Figure 8B:
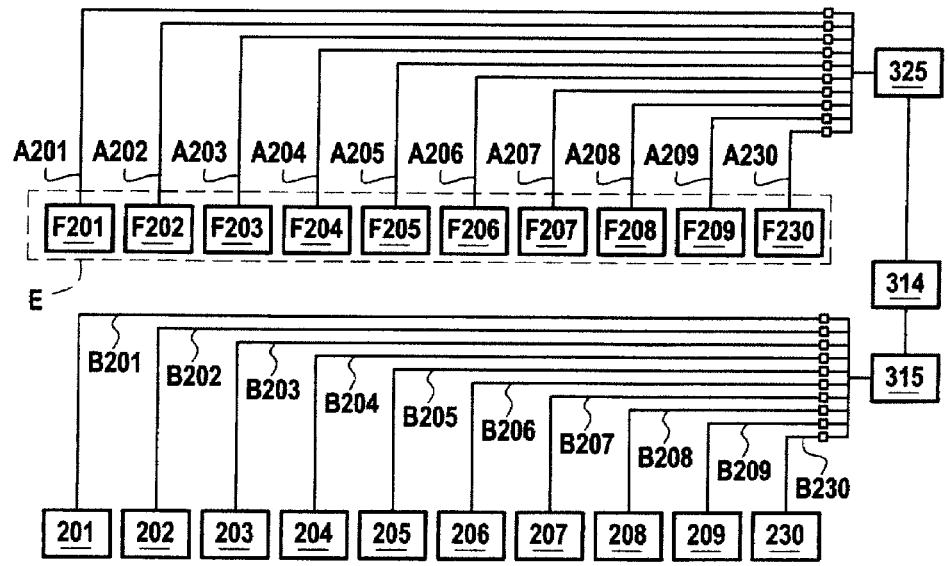
FIG. 8B shows details of the electrical connections of the electrocardiograph of FIG. 8A.

FIG. 8B shows in detail:
the electrical connections B201-B209, B230 between the electrodes 201-209, 230 and the analog-to-digital converter 315;
the electrical connection between the analog-to-digital converter 315 and the memory 314;
the electrical connection between the memory 314 and the digital-to-analog converter 325; and the electrical connections A201-A209, A230 between the digital-to-analog converter 325 and the sockets F201-F209, F230.

Figure 9:
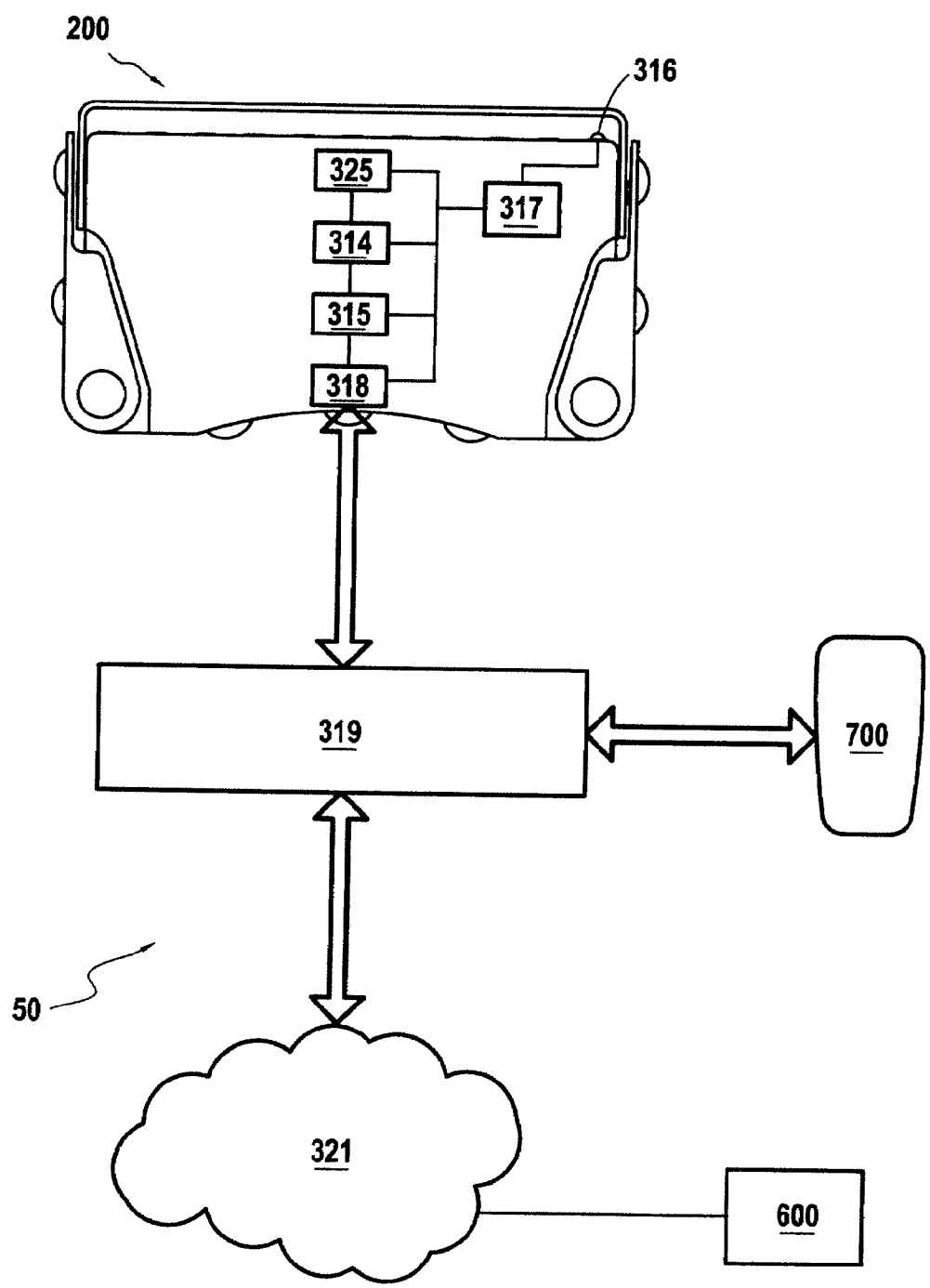
FIG. 9 shows a system in accordance with the invention for remotely monitoring the cardiac activity of a patient.

FIG. 9 shows a system in accordance with the invention for remotely monitoring the cardiac activity of a patient. The system 50 mainly comprises an electrocardiograph 200 constituting a particular embodiment of the invention, a Bluetooth (registered trademark) base 319 connected to a telecommunications network 321, and a medallion 700 suitable for establishing a Bluetooth connection via the base 319 with an operator located at a remote center 600.

By way of example, the patient may wear the medallion 700 about the neck, as shown in FIG. 7.

In the presently-described electrode, the electrocardiograph 200 has the same general structure as a computer. In particular, it includes a processor 317 and telecommunications means 318 suitable for establishing a Bluetooth (registered trademark) connection with the base 319.

In the presently-described electrode, the electrocardiograph 200 has ten electrodes similar to the above-described electrodes 201 to 209 and 230, each of these electrodes being connected to a rewritable non-volatile memory 314 via an electrical connection B201-B209, B230, as shown in FIG. 8B.

In the presently-described electrode, in order to avoid recording signals that have not stabilized, the processor 317 is suitable for determining whether the signals acquired by the electrodes are in conformity, and if so for storing these signals in the memory 314 after they have been converted by an analog-to-digital converter 315 as described above.

To this end, the processor 317 determines whether the analog signals acquired by the electrodes are characteristic of a QRS complex.

In the presently-described embodiment, the processor 317 is suitable for filtering the signals that are found to be in conformity by implementing the Pan Tompkins algorithm. It also stores the filtered signals in the memory 314.

In the presently-described embodiment, the event-driven ambulatory electrocardiograph 200 of the invention displays a message on the screen 250 shown in FIG. 3 indicating whether the electrodes are properly and/or wrongly positioned.

In the presently-described embodiment, the processor 317 triggers transmission of the signals stored in the memory 314 to the remote center 600 once the signals have been filtered.

In a variant, it could transmit the signals detected as being in conformity, prior to filtering.

For this purpose, it establishes a Bluetooth (registered trademark) connection between its communications means 318 and the base 319, with the base relaying the signals to the remote center 600.

In another embodiment, the electrocardiograph 200 may be configured not to transmit the signals to the remote processor 600 automatically, with the processor 317 always checking said configuration prior to triggering a transfer.

In the presently-described embodiment, the signals are conserved in the memory 314 so long as it is not saturated.

In the presently-described embodiment, the processor 317 is suitable for detecting reception of a command received from the remote center 600 via the Bluetooth base 319, and for responding to said command by transmitting to the remote center 600 the signals stored in the memory 314. This command may specify whether the signals for transmission are the signals in conformity before or after filtering.

In the presently-described embodiment, and as described with reference to the electrocardiograph of FIG. 8A to 8B, the electrocardiograph 200 has a set E of ten sockets F201-F209, F230 for outputting the signals obtained by the electrodes 201 to 209 and 230 to another electrocardiograph 300.

In the presently-described embodiment, the ten sockets F201-F209, F230 are also input sockets constituting so-called "secondary" means for obtaining a plurality of signals representative of the cardiac activity of a patient, these signals being acquired by another device, e.g. an electrode belt.

For this purpose, the strands 313 are used to convey the signals acquired by the other device to each of the sockets F201-F209, F230 of the electrocardiograph 200 of the invention, these strands being terminated by a connector 311 that is compatible with the sockets.

The signals obtained by the secondary means may be stored in the memory 314 or remotely transmitted to the remote center 600 via the base 319.

The invention claimed is:

1. An event-driven ambulatory electrocardiograph adapted to capture a twelve-lead electrocardiogram from analog electrical signals representative of the cardiac activity of a patient and acquired by means of at least nine electrodes, said electrocardiograph comprising a frontal face forming a body of said electrocardiograph provided with two precordial electrodes and two arms on either side of said body, each arm being provided with two precordial electrodes, each arm forming an angle relative to the frontal face such that the frontal face and the two arms define a surface that is substantially concave, wherein:
each arm is capable of being folded beside said body and is pivotable about an axis ($\Delta$, $\Delta'$) that is substantially parallel to said front face;
said arm being adapted to form a variable dihedral angle ($\phi$, $\Psi$) relative to said front face such that said substantially concave surface can adapt to the patient's morphology in order to enable said precordial electrodes to be properly positioned on the chest of said patient; and
in that said electrocardiograph includes means enabling said proper positioning of said precordial electrodes on the chest of said patient to be maintained, said means comprising a spring associated with each arm of said electrocardiograph, each spring being fastened via one end to the body of the electrocardiograph and via an opposite end to the arm with which the spring is associated.

2. An event-driven ambulatory electrocardiograph according to claim 1, characterized in that:
the two precordial electrodes of one of said arms correspond respectively to the points V1 and V2 of the patient's chest;
the two precordial electrodes of the other one of said arms correspond respectively to the points V5 and V6 of the patient's chest; and
the front face of the body of said electrocardiograph is provided with two precordial electrodes corresponding respectively to the points V3 and V4 of the patient's chest.

3. An event-driven ambulatory electrocardiograph according to claim 2, characterized in that:
it further includes amongst said nine electrodes, two electrodes enabling signals to be acquired relating to the upper limbs of said patient;
said two electrodes are disposed on said electrocardiograph in such a manner as to enable the index or middle fingers of said patient to be applied on said two electrodes when said six precordial electrodes are in position on the chest of said patient;

it further includes amongst said nine electrodes, a spoon or paddle type electrode located at the end of a cord attached to said electrocardiograph and enabling the signal to be acquired that relates to the lower left limb of said patient;

it further includes, in addition to said nine electrodes, a neutral electrode positioned on said front face of said body of said electrocardiograph so as to be applied beneath the left nipple of said patient;

said means enabling said precordial electrodes to be maintained properly positioned comprise a respective spring associated with each arm of said electrocardiograph;

for each of said electrodes, it includes:
means for converting the analog signal acquired by said electrode into a digital signal;
means for storing said digital signal; and
means for converting said digital signal into an analog signal and means for directing said analog signal to a socket compatible with a first connector of a strand having a second connector that is compatible with a second electrocardiograph;

it includes:
means suitable for determining whether said analog signals have characteristics corresponding to at least one QRS complex, with such signals being said to be "in conformity"; and
a memory suitable for storing said signals in conformity;

it includes means for filtering said signals in conformity;

it includes:
telecommunications means suitable for transmitting said signals in conformity or said filtered signals to a remote center from said memory; and
control means suitable for triggering said transmission on detecting at least one predetermined event;

said control means are suitable for triggering said transmission as soon as said signals have been determined as being in conformity, or as soon as they have been filtered;

said control means are adapted to configure said transmission on said electrocardiograph receiving a command for that purpose;

said control means are suitable for preventing said transmission;

it includes secondary means for obtaining a plurality of signals representative of the cardiac activity of a patient and coming from another device; and said secondary means comprise a plurality of sockets, each socket being compatible with a connector for conveying the analog signal obtained by said device.

4. An event-driven ambulatory electrocardiograph according to claim 3, further including means for displaying a message representative of proper and/or wrong positioning of the electrodes.

5. An event-driven ambulatory electrocardiograph according to claim 1, characterized in that it further includes amongst said nine electrodes, two electrodes enabling signals to be acquired relating to the upper limbs of said patient.

6. An event-driven ambulatory electrocardiograph according to claim 5, characterized in that said two electrodes are disposed on said electrocardiograph in such a manner as to enable the index or middle fingers of said patient to be applied on said two electrodes when said six precordial electrodes are in position on the chest of said patient.

7. An event-driven ambulatory electrocardiograph according to claim 1, characterized in that it further includes amongst said nine electrodes, a spoon or paddle type electrode located at the end of a cord attached to said electrocardiograph and enabling the signal to be acquired that relates to the lower left limb of said patient.

8. An event-driven ambulatory electrocardiograph according to claim 1, characterized in that it further includes, in addition to said nine electrodes, a neutral electrode positioned on said front face of said body of said electrocardiograph so as to be applied beneath the left nipple of said patient.

9. An event-driven ambulatory electrocardiograph according to claim 1, characterized in that, for each of said electrodes, it includes:
means for converting the analog signal acquired by said electrode into a digital signal;
means for storing said digital signal; and
means for converting said digital signal into an analog signal and means for directing said analog signal to a socket compatible with a first connector capable of connection to a second electrocardiograph.

10. An ambulatory event-driven electrocardiograph according to claim 1, characterized in that it includes:
means suitable for determining whether said analog signals have characteristics corresponding to at least one QRS complex, with such signals being said to be "in conformity"; and
a memory suitable for storing said signals in conformity.

11. An ambulatory event-driven electrocardiograph according to claim 10, characterized in that it includes means for filtering said signals in conformity.

12. An ambulatory event-driven electrocardiograph according to claim 10, characterized in that it includes:
telecommunications means suitable for transmitting said signals in conformity or said filtered signals to a remote center from said memory; and
control means suitable for triggering said transmission on detecting at least one predetermined event.

13. An electrocardiograph according to claim 12, characterized in that said control means are suitable for triggering said transmission as soon as said signals have been determined as being in conformity, or as soon as they have been filtered.

14. An electrocardiograph according to claim 12, characterized in that said control means are adapted to configure said transmission on said electrocardiograph receiving a command for that purpose.

15. An electrocardiograph according to claim 12, characterized in that said control means are suitable for preventing said transmission.

16. An electrocardiograph according to claim 1, characterized in that it includes secondary means for obtaining a plurality of signals from another device that previously collected signals representative of the cardiac activity of a patient.

17. An electrocardiograph according to claim 16, characterized in that said secondary means comprise a plurality of sockets, each socket being compatible with a connector for conveying the analog signal obtained by said device.

18. An event-driven ambulatory electrocardiograph according to claim 1, further including means for displaying a message representative of proper and/or wrong positioning of the electrodes.

19. A system for remotely monitoring the cardiac activity of a patient, the system comprising:
an electrocardiograph according to claim 12, in which said telecommunications means are constituted by means for wireless telecommunication with a base connected to a telecommunications network; and
said base.

20. A monitoring system according to claim 19, characterized in that it further includes portable equipment suitable for establishing voice communication with a remote operator via said base.

21. A system for remotely monitoring the cardiac activity of a patient, the system comprising:
an electrocardiograph according to claim 4, in which said telecommunications means are constituted by means for wireless telecommunication with a base connected to a telecommunications network; and
said base.

22. A monitoring system according to claim 21, characterized in that it further includes portable equipment suitable for establishing voice communication with a remote operator via said base.

* * * * *